United States Patent [19]

Makino et al.

[11] Patent Number: 5,350,675
[45] Date of Patent: Sep. 27, 1994

[54] MULTILAYER ANALYTICAL ELEMENT FOR DETERMINATION OF TOTAL CHOLESTEROL IN BLOOD

[75] Inventors: Yoshihiko Makino; Kaoru Terashima, both of Saitama, Japan

[73] Assignee: Fuji Photo Film Co., Ltd., Kanagawa, Japan

[21] Appl. No.: 942,099

[22] Filed: Sep. 8, 1992

Related U.S. Application Data

[63] Continuation of Ser. No. 460,827, Jan. 4, 1990, abandoned.

[30] Foreign Application Priority Data

Jan. 6, 1989 [JP] Japan ..................... 64-1070

[51] Int. Cl.$^5$ .................. C12Q 1/60; G01N 21/00; G01N 1/00
[52] U.S. Cl. ........................ 435/11; 422/56; 422/57; 436/174; 436/175; 436/177
[58] Field of Search ................ 435/11.19; 436/174, 436/175, 177; 422/56, 57

[56] References Cited

U.S. PATENT DOCUMENTS

| | | | |
|---|---|---|---|
| 2,541,991 | 2/1951 | DeGroote | 252/342 |
| 3,925,164 | 12/1975 | Beaucamp | 195/103.5 R |
| 3,992,158 | 11/1976 | Przybylowicz | 23/253 |
| 4,144,129 | 3/1979 | Gruber | 195/66 R |
| 4,202,938 | 5/1980 | Haeckel | 435/10 |
| 4,212,938 | 7/1980 | Gruber | 435/11 |
| 4,258,001 | 3/1981 | Pierce | 422/56 |
| 4,275,151 | 6/1981 | Esders | 435/11 |
| 4,292,272 | 9/1981 | Kitajima | 422/57 |

FOREIGN PATENT DOCUMENTS 3823347 3/1961 Japan .

*Primary Examiner*—Michael G. Wityshyn
*Assistant Examiner*—Ralph Gitomer
*Attorney, Agent, or Firm*—McAulay Fisher Nissen Goldberg & Kiel

[57] ABSTRACT

In a dry type analytical element having at least one water-permeable layer including a porous spreading layer and at least one water-permeable layer, containing an enzyme having cholesterol esterase activity, the improvement which comprises containing a condensate of poly(ethylene oxide) monoalkylphenyl ether and formaldehyde at least in the water-permeable layer containing the enzyme or another water-permeable layer. In the analytical element of the invention, hemolysis does not occur and bound cholesterol is sufficiently decomposed to free cholesterol.

9 Claims, No Drawings

MULTILAYER ANALYTICAL ELEMENT FOR DETERMINATION OF TOTAL CHOLESTEROL IN BLOOD

This is a continuation of application Ser. No. 460,827, filed Jan. 4, 1990, now abandoned.

BACKGROUND OF THE INVENTION

1. Field of the Invention

This invention relates to a dry-type integral multilayer analytical element for the quantitative analysis of total cholesterol in a blood sample.

2. Description of the Prior Art

The total cholesterol in blood consists of bound cholesterol and free cholesterol. The free cholesterol occupies only about 25% of the total cholesterol, and the bound cholesterol occupies about 75%. The bound cholesterol is a complex of cholesterol ester and protein. The free cholesterol can be analyzed quantitatively by oxidizing in the presence of cholesterol oxidase and then determining the produced hydrogen peroxide or cholestenone, but the bound cholesterol cannot be analyzed unless it is decomposed to free cholesterol.

Since the complex of cholesterol ester and protein inhibits the action of cholesterol esterase on cholesterol ester, it is necessary to decompose the complex prior to allowing the esterase to act. As such a means, it is proposed to allow polyethylene oxide monoalkylphenyl ether (alkylphenoxypolyethoxyethanol (synonym)) having an ethylene glycol unit of less than 20 to act (U.S. Pat. Nos. 4,275,151, 4,275,152). It is also known to use a surfactant such as polyethylene glycol alkylether together with cholesterol esterase (U.S. Pat. No. 3,925,164).

On the other hand, in clinical chemical assay analyzing blood samples, it is desirable to conduct accurate analysis by using a small amount of the samples. Heretofore, wet analyses using liquid reagents were widely utilized, but it is inferior in rapidity. While, dry analyses, i.e. the clinical assays using an analytical element substantially in a dry state such as a test piece or a multilayer analytical element containing an analytical reagent system, have been developed since the period of nineteen seventies. The dry analyses are superior to the wet analyses in simple operations, rapidity and low cost. Dry type multilayer analytical elements were developed as an analytical means capable of conducting accurate analysis rapidly using a small amount of samples (U.S. Pat. Nos. 3,992,158, 4,292,272, EP 0 162 302 A, etc.). The dry type multilayer analytical element is constructed, for example, by a transparent support, a reagent layer, a light reflecting layer and a spreading layer. The support is made of a thin plastic film or sheet. The reagent layer coated on the support contains a reagent system reacting with the analyte in a liquid sample to color in an optical density corresponding to the amount of the analyte. The light reflecting layer prevents that the light incident to the reagent layer reaches the spreading layer, and thereby, the influence of the colored liquid sample spotted onto the spreading layer is excluded at the time of the optical measurement of the reagent layer. The spreading layer spreads the liquid sample spotted thereto uniformly into an area in proportion to the liquid amount. When a quantitative analysis is conducted using the above dry type analytical element, a definite amount of a liquid sample such as a whole blood sample is spotted to the surface of the spreading layer. The sample spread in the spreading layer permeates the light reflecting layer to reach the reagent layer. The analyte reacts with the reagent to color or to change color. After spotting, the color reaction is allowed to proceed sufficiently by keeping the analytical element at a definite temperature (incubation) for a suitable time, and then, a light is irradiated to the reagent layer from the transparent support side to determine the reflection optical density by measuring the amount of the reflected light in a restricted wave region. The amount of the analyte can be determined by using a calibration curve which has previously been prepared.

In the past, most of blood samples were treated with the removal of erythrocytes, and the blood sera or blood plasmas thus obtained were subjected to analysis, irrespective of wet analysis or dry analysis. Since the removal of erythrocytes is difficult and requires costly equipment, it is preferred to analyze undiluted whole blood samples as is.

In order to analyze a whole blood sample by dry analysis, it is necessary to separate the blood serum or plasma from blood cells in the analytical element. The dry type analytical element disclosed in EP 0 226 465 A satisfies these requirements and is useful for the analysis of a particular component in a whole blood sample. The analytical element contains a first nonfibrous porous layer, a second nonfibrous porous layer and a fibrous porous layer integrally superposed in this order, and the respective layers are laminated closely by an adhesive partially disposed to form microspaces so as not to interfere uniform permeation of liquid. A reagent composition to produce an optical change such as coloring is incorporated in one or more of the above three layers, and the optical change caused by an analyte is detected mainly at the first nonfibrous porous layer. In the multilayer analytical element, the second nonfibrous porous layer and the fibrous porous layer works cooperatively to remove blood cell components from blood sample.

In the above multilayer analytical element having the layers for separating blood cells at the upper part, the hemolysis in the layers for separating blood cells is a great problem. That is, the hemoglobins or the like are released from red blood cells by the hemolysis, and interfere with the measurement of reflected light in a restricted region. Moreover, the hemolysis changes the total cholesterol concentration of blood sera or plasmas. Sometimes, enzyme reaction or coloring reaction is inhibited by the hemolyzed products. Thus, when hemolysis occurs in an analytical element, particularly in a layer for separating blood cells, the hemolysis reduces the accuracy of the total cholesterol analysis.

The aforementioned polyethylene oxide monoalkylphenyl ether is useful for the hydrolysis of cholesterol, but this compound has a great hemolyzability. Moreover, since the compound is a relatively low molecular weight, its diffusibility to other layers is great. Therefore, when the compound is incorporated into a dry type analytical element having a layer for separating blood cells, hemolysis occurs in the analytical element. As a result, the analysis of total cholesterol concentration cannot be conducted accurately.

SUMMARY OF THE INVENTION

An object of the invention is to provide an analytical element for total cholesterol in which hemolysis does not occur but bound cholesterol is sufficiently decomposed to free cholesterol.

In order to achieve the above object, the inventors attemped to use the increased polymerization degree of the hydroxyethylene unit of polyethylene oxide monoalkylphenyl ether greater than 40. However, when the above polyethylene oxide monoalkylphenyl ether was used, the ability to decompose bound cholesterol decreased, though the hemolizability reduced. As a result, the analysis of total cholesterol concentration was still inaccurate. Then, they further investigated, and succeeded to complete an analytical element which has achieved the above object.

Thus, the present invention provides a dry type analytical element having at least one water-permeable layer including a porous spreading layer and at least one water-permeable layer containing an enzyme having cholesterol esterase activity, which comprises containing a condensate of poly(ethylene oxide) monoalkylphenyl ether and formaldehyde at least in the water-permeable layer containing the enzyme or another water-permeable layer.

DETAILED DESCRIPTION OF THE INVENTION

The analytical element of the invention has at least one water-permeable layer and at least one of the water-permeable layers is a porous spreading layer.

The water-permeable layers include a hydrophilic polymer layer, a porous reagent layer and a blood cell-separating layer as well as the porous spreading layer.

The analytical element of the invention may have a light-transmissive support which is preferably water-impermeable. Moreover, preferred embodiments have at least one porous reagent layer and one blood cell-separating layer for separating blood cell components from blood. In this construction, it is preferred to interpose at least one hydrophilic polymer layer between the light-transmissive water-impermeable support and the porous layer.

The hydrophilic polymer layer is a substantially uniform layer containing a hydrophilic polymer as a binder. Suitable hydrophilic polymers include gelatin, gelatin derivatives such as phthalated gelatin, cellulose derivatives such as hydroxypropylcellulose, agarose, polyacrylamide, polymethacrylamide and copolymers of acrylamide or methacrylamide and various vinyl monomers.

The porous reagent layer may be a fibrous porous layer composed of filter paper, nonwoven fabric or the like or a nonfibrous porous layer. Suitable nonfibrous porous layers are blushed polymer layers composed of a cellulose ester such as cellulose acetate, cellulose acetate/butyrate or cellulose nitrate disclosed in U.S. Pat. Nos. 3,992,158 and 1,421,341, microporous membranes composed of polyamide such as 6-nylon or 6,6-nylon, polyethylene or polypropylene, microporous membranes composed of polysulfone disclosed in CA 106, 140219k (1987), porous layers having continuous microspaces formed by binding polymer particulates, glass particulates or diatomaceous earth with a hydrophilic or non-water-absorptive polymer disclosed in U.S. Pat. Nos. 3,992,158 and 4,258,001 and polymer particulate constructions disclosed in CA 97, 159156e and U.S. Pat. No. 4,430,436. Among them, the blushed polymer layers are preferred. In the membrane filter of the blushed polymer prepared by the phase separation method, the liquid passes in the cross direction are the narrowest on the free surface side during manufacturing the membrane, i.e. glossy face. When the membrane filter of the blushed polymer is used for the porous reagent layer, it is preferred to dispose the glossy face on the side of the support. The porous reagent layer may functions as the spreading layer of the blood serum or plasma separated from a blood sample. The spreading, in this case, means to spread the blood serum or plasma almost uniformly into an extent broader than the spread area through the porous spreading area and the blood cell-separating layer.

The blood cell-separating layer includes a composite porous layer composed of a fibrous porous layer and a nonfibrous porous layer laminated to each other through an adhesive partly disposed so as to pass a liquid uniformly. The fibrous porous layer is disposed on the side opposite to the support.

The nonfibrous porous layer usable for the blood cell-separating layer includes nonfibrous isotropically porous layers such as membrane filters (blushed polymer layers) disclosed in U.S. Pat. Nos. 3,992,158 and 1,421,341, polyolefin microporous membrane disclosed in "The 9th Plastic Film Kenkyu-Kai Koza Koen Yoshi-Shu (Summaries of Lectures in The 9th Plasitic Film Research Meeting Course Lecture)" (Kobunshi Gakkai, published on Feb. 22, 1984) and Membrana, Inc, Catalogue (published in July, 1982), continuous microspace-containing porous layers disclosed in U.S. Pat. No. 3,992,158, continuous microspace-containing porous layers (three-dimensional lattice particulate structure layers) disclosed in U.S. Pat. No. 4,258,001 and the like. The membrane filters are composed of cellulose ester such as cellulose acetate, cellulose butyrate, cellulose acetate bytyrate (ester mixture) or cellulose nitrate, cellulose ether such as ethyl cellulose, carbonate ester polymer such as polycarbonate of bisphenol A, polyamide such as polycapramide (6-nylon) or polyhexamethyleneadipamide (6,6-nylon), or the like. The polyolefin microporous membranes includes polyethylene microporous membrane and polypropylene microporous membrane. The former continuous microspace-containing porous layers are composed of polymer particulates glass particulates, diatomaceous earth or other particulates binded through a hydrophilic polymer, and the latter continuous microspace-containing porous layers are composed of polymer particulates joined so as to contact with each other at a point using a polymer adhesive. The nonfibrous porous layer has a void size (mean minimum pore size) of about 0.8 to about 30 $\mu$m, preferably about 1 to about 10 $\mu$m, a void content of about 20 to about 90%, preferably about 40 to about 85%, and a thickness of about 20 to about 500 $\mu$m, preferably about 80 to about 350 $\mu$m.

The fibrous porous layer may be selected from the fibrous porous materials for the porous spreading layer described later.

The lamination of the fibrous porous layer to the nonfibrous porous layer may be conducted according to the method disclosed in EP 0 226 465 A or the like. Preferable adhesives include hot melt-type adhesives.

In the blood cell-separating layer, the above two layers filter off blood cells and also act spreading action under their cooperation.

The porous spreading layer preferably has a liquid metering action. The liquid metering action means that the liquid sample spotted on the surface of this layer uniformly spreads along in all directions of the surface of the spreading layer at the rate of approximately equal amount per unit area without uneven distribution of any component. The material constructing the porous spreading layer may be a fibrous porous material such as filter paper, nonwoven fabric, woven fabric such as plain weave fabric, knitted fabric such as tricot cloth, glass fiber filter paper or the like. There can be used a composite membrane filter (composite blushed polymer layer) having a communicating void structure formed by closely bonding two layers of microporous high-molecular material layer at the interface therebetween, said layers being formed by a multilayer coating method or a multilayer casting method, instead of using said two non-fibrous porous layers bonded by adhesive layers having a communicating micropore structure. Among them, woven fabrics and knitted fabrics are preferred. The woven fabrics and knitted fabrics may be treated with glow discharge disclosed in GB 2 087 074 A. Hydrophilic polymers or surfactants disclosed in EP 0 162 301 A and Japanese Patent KOKAI Nos. 63-219397, 63-112999 and 62-182652 may be incorporated into the spreading layer in order to control spreading area, spreading speed or the like. When the analytical element of the invention contains the blood cell-separating layer, the porous spreading layer is a part of the blood cell-separating layer. In this case, the layer functioning as the porous spreading layer is preferably disposed on the opposite side to the support.

The analytical element of the invention may contain other layers. For example, a barrier layer such as disclosed in Research Disclosure, No. 12626, pp 51-56, 1974 may be incorporated between the porous reagent layer and the hydrophilic polymer layer.

In the analytical element of the invention, at least one of the water-permeable layer contains an enzyme having cholesterol esterase activity (CHE). CHE is used for producing free cholesterol from cholesterol ester, and includes cholesterol esterases disclosed in U.S. Pat. Nos. 3,925,164 and 4,275,151 and various commercial cholesterol esterases. The cholesterol esterases may be animal origin, microbial origin or the like. Lipoprotein lipase may be added together with CHE as disclosed in Japanese Patent KOKOKU No. 56-19240.

When the analytical element of the invention is used for the quantitative analysis of total cholesterol, the analytical element further contains cholesterol oxidase and a reagent composition producing a detectable optical change in the presence of hydrogen peroxide.

Cholesterol oxidases are, for example, disclosed in U.S. Pat. Nos. 4,144,129 and 4,008,127, and they are usable for the invention.

The reagent composition producing a detectable optical change in the presence of hydrogen peroxide is selected according to the analytical method for determining hydrogen peroxide employed in the analytical element. Such a reagent composition includes a combination of peroxidase and 4-aminoantipyrine and naphthols disclosed in U.S. Pat. No. 3,983,005, a combination of peroxidase, a hydrogen donor and a N,N-disubstituted aniline disclosed in U.S. Pat. No. 4,478,942, a reagent system to produce a dye through oxidation of a leuco dye such as a combination of peroxidase and imidazole leuco dyes disclosed in U.S. Pat. No. 4,089,747 and EP 0 122 641 A, and the like.

Instead, free cholesterol can be determined by the method of using a NAD- or NADP-dependent cholesterol dehydrogenase to determine the produced cholestenone or NADH or NADPH. Cholestenone can be determined by using hydrazines such as hydrazine or 2,4-dinitrohydrazine.

The reagent composition optionally contains an activator, a buffer, a curing agent, a surfactant or the like. Suitable buffers are carbonates, borates, phosphates, the Good's buffers disclosed in Biochemistry, vol. 5, No. 2, pp 467–477, 1969. The buffers can be selected in reference to Horio et al., "Tanpakushitsu . Koso no Kisojikken Ho (Fundamental Experimental Method of Proteins and Enzymes)", Nanko-Do, 1981, the above Biochemistry, and the like.

The analytical element of the invention is characterized by incorporating a condensate of poly(ethylene oxide) monoalkylphenyl ether and formaldehyde.

The polyethylene oxide monoalkylphenyl ether composing the condensate has a polyethylene oxide chain having a number of hydroxyethylene unit of preferably not more than 20, and a preferred condensate is composed of 2 to 4 molecules of the polyethylene oxide monoalkylphenyl ether condensed with formaldehyde.

Preferred condensates are represented by the following general formula [I]:

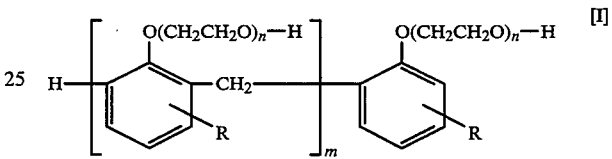

wherein m is an integral number of 2 to 4, n is an integral number of not more than 20, preferably 7 to 12, and R is an alkyl group having a number of carbon atoms of 4 to 12.

Preferred alkyl groups of R are straight chain or branched chain having a number of carbon atoms of 8 or 9.

The condensate of polyethylene oxide monoalkylphenyl ether and formaldehyde can be synthesized by a known method such as disclosed in U.S. Pat. No. 2,541,991 where a condensate of an alkylphenol and formaldehyde is allowed to react with an alkylene oxide to produce the object condensate through hydroxyalkylation. The method disclosed in Japanese Patent KOKOKU No. 38-23347 is also usable.

The condensate is incorporated into at least one water-permeable layer. CHE may be incorporated into another water-permeable layer, but to incorporated into the same layer as the condensate is preferred.

When the analytical element is used for the quantitative analysis, cholesterol oxidase and the reagent composition producing a detectable optical change may be incorporated into the porous reagent layer together with CHE, or a part of them may be incorporated into another water-permeable layer. For example, CHE and cholesterol oxidase are incorporated into the porous reagent layer and the reagent composition is incorporated into the hydrophilic polymer layer. CHE may be incorporated into the blood cell-separating layer. Respective reagent components may be incorporated into two or more layers. For example, the part of the reagent composition to produce an intermediate through the reaction with free cholesterol is incorporated into the porous reagent layer, and the part to react with the intermediate to produce a dye is incorporated into the hydrophilic polymer layer.

The analytical element of the invention can be prepared according to a conventional method. As an embodiment, the reagent composition may substantially be incorporated into the porous reagent layer by coating an uniform layer containing the reagent composition and a hydrophilic polymer as binder and then joining a nonfibrous porous layer not containing the reagent composition by the method disclosed in U.S. Pat. No. 4,292,272.

EXAMPLES

Example 1

1-1 Preparation of Leuco Dye Emulsion

The following leuco dye solution was prepared.

| | |
|---|---|
| 2-(4-hydroxy-3,5-dimethoxyphenyl)-4-[4-(dimethylamino)phenyl]-5-phenethylimidazole acetate | 5.7 g |
| 2-(4-hydroxy-3,5-dimethoxyphenyl)-4-[4-(dimethylamino)phenyl]-5-phenethylimidazole hydrochloride | 0.8 g |
| N,N-diethyllaurylamide | 104 g |
| The following gelatin solution was prepared. | |
| Alkali-treated gelatin | 300 g |
| Water | 1900 g |
| Bis[(vinylsulfonylmethylcarbonyl)amino]methane | 3.0 g |

The gelatin solution was stirred by an emulsifier at about 5,700 rpm, and the leuco dye solution was added. The mixture was stirred for about 30 minutes to obtain the emulsion.

1-2 Coating of Dye-Forming Reagent Layer

The above emulsion was coated on the support of a gelatin-subbed transparent polyethylene terephthalate (PET) film 180 μm in thickness at a rate of 150 g/m$^2$, and dried to form a dye-forming reagent layer.

1-3 Lamination of First Porous Layer

The surface of the dye-forming reagent layer was moistened uniformly with about 30 g/m$^2$ of water at 25° C. A cellulose acetate membrane filter ("MICROFILTER FM 300", manufactured by Fuji Photo Film Co., Ltd.) having an effective pore size of 1.2 μm, a thickness of 140 μm and a void content of about 80% was superposed thereon, and dried to laminate the membrane filter to the dye-forming reagent layer.

Subsequently, the following composition was applied at a rate of 110 ml/m$^2$ onto the membrane filter, and dried to obtain the first porous layer.

| | |
|---|---|
| Water | 1233 g |
| Cholesterol esterase | 1.7 g |
| Cholesterol oxidase | 10.18 g |
| Lipoprotein lipase | 1.94 g |
| Peroxidase | 8.86 g |
| Potassium ferrocyanide | 5.6 g |
| Condensate of general formula [I] (Mixture of R = p-nonyl, n = 10, m = 2 and 3) | 4.6 g |

1-4 Impregnation of Second Porous layer and Spreading Layer

A cellulose acetate membrane filter ("MICROFILTER FM 300", manufactured by Fuji Photo Film Co., Ltd.) having an effective pore size of 3 μm, a thickness of 140 μm and a void content of about 80% was used for the second porous layer, and a tricot fabric about 250 μm thick knitted from 50 deniers PET spun yarn by 36 gauges was used for the spreading layer. The membrane filter and the tricot fabric were immersed in an aqueous solution containing 2 wt. % of the condensate mixture of the general formula [I] where R is p-nonyl group, n=10 and m=2 and 3. After the void portions of them were filled with the solution, they were taken out and dried.

1-5 Lamination of Second Porous Layer and Spreading Layer

The impregnated tricot fabric was heated at 80° C., and hot melt type adhesive melted at 130° C. was adhered to the surface of the tricot fabric in dot-shaped by the transferring from a gravure roll utilizing the gravure printing. The distance between each center of the dots was 0.9 mm, the area of the dots was about 20%, and the adhered hot melt type adhesive wa about 3 g/m$^2$. The nonglossy side of the membrane filter was immediately faced to the tricot fabric, and both were joined through the dot-shaped adhesive by passing a laminating roller.

The laminate was laminated to the first porous layer in a similar manner to the above method. That is, a hot melt type adhesive was adhered in dot-shaped to the membrane filter face of the above laminate by the transferring from a gravure roll utilizing the gravure printing, and immediately faced to the face of the first porous layer, and joined them through the dot-shaped adhesive by passing a laminating roller.

Thus, an integral multilayer analytical element for the quantitative analysis of total cholesterol was completed. The analytical element consisted of a support, a dye-forming reagent layer, a first porous layer, a second porous layer and a spreading layer laminated in this order. The spreading layer and the second porous layer act as the blood cell-separating layer cooperatively. The first porous layer acts as an reaction layer to produce ferric ion in the presence of cholesterol. In the dye-forming reagent layer, a dye is produced by the ferric ion produced in the first porous layer, and the dye is optically measured through the transparent support.

1-6 Preparation of Analytical Slide

The analytical element was cut into square pieces having a side of 15 mm, and placed in a slide frame described in Japanese Patent KOKAI No. 57-63452 to complete an analytical slide for the quantitative analysis of total cholesterol.

COMPARATIVE EXAMPLE

An analytical slide for the quantitative analysis of total cholesterol was prepared in the same manner as Example 1, except that poly(ethylene oxide) mono-p-octylphenyl ether having the number of hydroxyethylene units of 10 was used instead of the condensate of the general formula [I].

Measurement of Total Cholesterol

Both of the above analytical slides were evaluated as follows: A human blood plasma sample containing 160 mg/dl of total cholesterol and a human whole blood sample having the same content of total cholesterol and a hematocrit value of 40% were used. Each 10 μl of the sample was spotted to the spreading layer of the analytical slide of Example 1 and Comparative Example 1, and incubated at 37° C. for 3 minutes and 6 minutes. Then, the reflection optical density of respective analytical slides was measured by using a light having a central wave length of 640 nm from the PET support side. The results are shown in Table 1. The numerical values in Table 1 are the percentage of the reflection optical density of the whole blood sample against the reflection optical density of the blood plasma sample.

TABLE 1

| Reaction Time | Example 1 | Comparative 1 |
| --- | --- | --- |
| 3 min | 98% | 38% |
| 6 min | 97% | 31% |

As shown in Table 1, in the case of the analytical slide of Example 1, similar reflection optical densities were obtained irrespective of a blood plasma sample or a whole blood sample. Whereas, in the case of the analytical slide of Comparative Example 1, the colored concentration o#the whole blood sample was sharply reduced compared with the blood plasma sample.

Hemolysis Test

To a whole blood sample, one of the surfactants shown in Table 2 was added, and stirred well. The whole blood sample was contrifuged at 5000 rpm for 10 minutes, and the absorbance at the central wave length of 575 nm of the supernatant was measured. Separately, the whole blood sample was hemolyzed completely by freezing, and the absorbance of the supernatant was measured in the same method. The relative value of the former absorbance to the latter absorbance which is set 100 is indicated in Table 2 as hemolyzed degree.

TABLE 2

| Surfactant | Hemolyzed Degree |
| --- | --- |
| Condensate employed in Example 1 | about 1 |
| Poly(ethylene oxide) mono-p-octylphenyl ether (n = 40) | about 1 |
| octylphenyl ether (n = 10) | 100 |
| None | 0 | n is the number of oxyethylene units

Decomposition Test of Bound Cholesterol

The following reagent solution for the quantitative analysis of total cholesterol was prepared.

| | |
| --- | --- |
| Water | 1000 ml |
| Cholesterol esterase | 4.0 U |
| Cholesterol oxidase | 4.0 U |
| Peroxidase | 10.0 U |
| 4-Aminoantipyrine | 2.0 mM |
| 1,7-Dihydroxynaphthalene | 4.0 mM |
| Poly(ethylene oxide) mono-p-octylphenyl ether The number of hydroxyethylene units; 10 | 20 g |
| Sodium phosphate buffer (pH 6.8) | 67 mM |

Each 20 μl of cholesterol standard solutions different in the total cholesterol concentration was added to 3 ml of the above reagent solution, and incubated at 37° C. for 10 minutes to prepare a calibration curve. Subsequently, the poly(ethylene oxide) mono-p-octylphenyl ether was replaced by one of the surfactants shown in Table 2, and a human blood plasma sample containing 160 mg/dl of total cholesterol was added. Then, the mixture was incubated in the same manner as above, and the total cholesterol concentration was calculated by using the above calibration curve. The results are shown in Table 3.

TABLE 3

| Surfactant | Total Cholesterol Concentration mg/dl | Detected Ratio % |
| --- | --- | --- |
| Condensate employed in Example 1 | 160 | 100 |
| Poly(ethylene oxide) mono-p octylphenyl ether (n = 40) | 37 | 23 |
| octylphenyl ether (n = 10) | 160 | 100 |
| None | 2.6 | 1.6 |

As shown in Table 3, bound cholesterol was not sufficiently decomposed by poly(ethylene oxide) mono-p-octylphenyl ether having a great number of hydroxyethylene units such as 40. In contrast, the condensate of poly(ethylene oxide) monoalkylphenyl ether and formaldehyde of the invention decomposed bound cholesterol sufficiently comparative with poly(ethylene oxide) mono-p-octylphenyl ether having a small number of hydroxyethylene units such as 10.

The above results of the hemolysis test and the decomposition test indicate that poly(ethylene oxide) monoalkylphenyl ether having a small number of hydroxyethylene units has a sufficient ability to decompose bound cholesterol, but greatly hemolyze whole blood. However, poly(ethylene oxide) monoalkylphenyl ether having a great number of hydroxyethylene units does not hemolyze, but its ability to decompose bound cholesterol is low. In contrast, the condensate of poly(ethylene oxide) monoalkylphenyl ether and formaldehyde has a sufficient ability to decompose bound cholesterol, but does not hemolyze.

We claim:

1. In a dry type integral multilayer analytical element for the quantitative analysis of total cholesterol having at least one hydrophilic polymer layer, one porous reagent layer and one blood cell-separating composite layer for separating blood cells from blood, laminated in this order onto a light-transmissive support, said blood cell-separating composite layer containing a porous spreading layer and containing at least one enzyme having cholesterol esterase activity, cholesterol oxidase and one reagent composition producing a detectable optical change in the presence of hydrogen peroxide, the improvement which comprises said porous reagent layer containing the at least one enzyme having cholesterol esterase activity or the cholesterol oxidase and wherein a part of the at least one hydrophilic layer, the porous reagent layer or the blood cell-separating composite layer contains a condensate represented by the general formula (I):

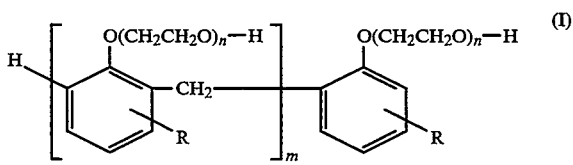

wherein m is an integral number of 2 to 4, n is an integral number of not more than 20, and R is an alkyl group having 4 to 12 carbon atoms.

2. The analytical element of claim 1 wherein R is p-nonyl, n is 10, and m is 2.

3. The analytical element of claim 1 wherein R is p-nonyl, n is 10, and m is 3.

4. The analytical element of claim 1 wherein the porous spreading layer is a part of the blood cell-separating composite layer and is positioned on the side of the blood cell-separating composite layer opposite to the support.

5. The analytical element of claim 1 wherein said blood cell-separating composite layer consists essentially of a fibrous porous layer disposed on the side of the blood cell-separating composite layer opposite to the support and a nonfibrous porous layer laminated to each other with an adhesive film which is discontinuous so as to pass a liquid uniformly.

6. The analytical element of claim 5 wherein both of said nonfibrous porous layer and porous reagent layer are blushed polymer layers.

7. The analytical element of claim 6 wherein each blushed polymer layer has a glossy face disposed such that each glossy face faces the support.

8. The analytical element of claim 1 wherein at least one of the porous reagent layer or the blood cell-separating composite layer contains the condensate represented by the general formula (I)

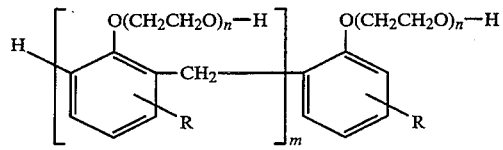

wherein m is an integral number of 2 to 4, n is an integral number of not more than 20, and R is an alkyl group having 4 to 12 carbon atoms.

9. The analytical element of claim 8 wherein both of the porous reagent layer and the blood cell-separating composite layer contain the condensate represented by the general formula (I)

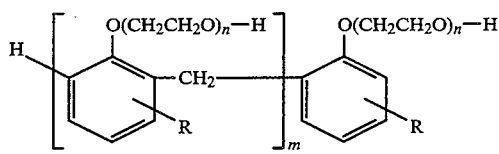

wherein m is an integral number of 2 to 4, n is an integral number of not more than 20, and R is an alkyl group having 4 to 12 carbon atoms.

* * * * *